(12) United States Patent
Bailey et al.

(10) Patent No.: US 7,798,999 B2
(45) Date of Patent: Sep. 21, 2010

(54) ADJUSTABLE LENGTH CATHETER

(75) Inventors: Frances Kristen Bailey, Bloomington, IN (US); Jessica L. Burke, Bloomington, IN (US); Grant T. Hoffman, Bloomington, IN (US); Ram H. Paul, Jr., Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/758,543

(22) Filed: Jun. 5, 2007

(65) Prior Publication Data

US 2008/0306465 A1  Dec. 11, 2008

(51) Int. Cl.
*A61M 5/178* (2006.01)

(52) U.S. Cl. .................. 604/164.05; 604/160; 604/161

(58) Field of Classification Search .................. 604/43, 604/160, 161, 164.05, 284, 523, 533, 164.06
See application file for complete search history.

(56) References Cited

U.S. PATENT DOCUMENTS

| | | | |
|---|---|---|---|
| 1,064,307 A | 6/1913 | Fleming | |
| 1,663,748 A | 3/1928 | Bender et al. | |
| 2,662,283 A | 12/1953 | Gienger | |
| 4,473,067 A | 9/1984 | Schiff | |
| 4,530,525 A | 7/1985 | Schneider | |
| 4,547,194 A | 10/1985 | Moorehead | |
| 4,631,059 A | 12/1986 | Wolvek et al. | |
| 4,687,469 A | 8/1987 | Osypka | |
| 4,743,265 A | 5/1988 | Whitehouse et al. | |
| 4,801,294 A | 1/1989 | Okada | |
| 4,887,997 A | 12/1989 | Okada | |
| 4,997,424 A * | 3/1991 | Little | 604/161 |
| 5,250,033 A | 10/1993 | Evans et al. | |
| 5,255,690 A | 10/1993 | Keith et al. | |
| 5,718,692 A * | 2/1998 | Schon et al. | 604/264 |
| 5,800,414 A * | 9/1998 | Cazal | 604/523 |
| 5,908,405 A * | 6/1999 | Imran et al. | 604/508 |
| 7,014,626 B2 | 3/2006 | Sanderson | |
| 2002/0111346 A1* | 8/2002 | Sodemann | 514/222.5 |
| 2002/0128607 A1* | 9/2002 | Haury et al. | 604/187 |
| 2005/0209582 A1 | 9/2005 | Quinn et al. | |
| 2005/0253390 A1 | 11/2005 | Blazek | |
| 2005/0256510 A1* | 11/2005 | Moskowitz et al. | 604/540 |
| 2007/0078438 A1* | 4/2007 | Okada | 604/523 |
| 2007/0225684 A1* | 9/2007 | Wentling et al. | 604/533 |

* cited by examiner

*Primary Examiner*—Kevin C Sirmons
*Assistant Examiner*—Emily Schmidt
(74) *Attorney, Agent, or Firm*—Brinks Hofer Gilson & Lione

(57) ABSTRACT

An adjustable length catheter device, a kit and a method of providing the adjustable length catheter device to a patient are provided. The catheter device includes an elongate shaft having a proximal portion, a distal portion, a first lumen and a second lumen extending at least partially therethrough. The catheter device further includes a manifold operably connected to the shaft. The manifold is configured to longitudinally move along the shaft towards the distal portion for separating the proximal portion of the shaft into a first proximal shaft portion including the first lumen and a second proximal shaft portion including the second lumen.

12 Claims, 8 Drawing Sheets

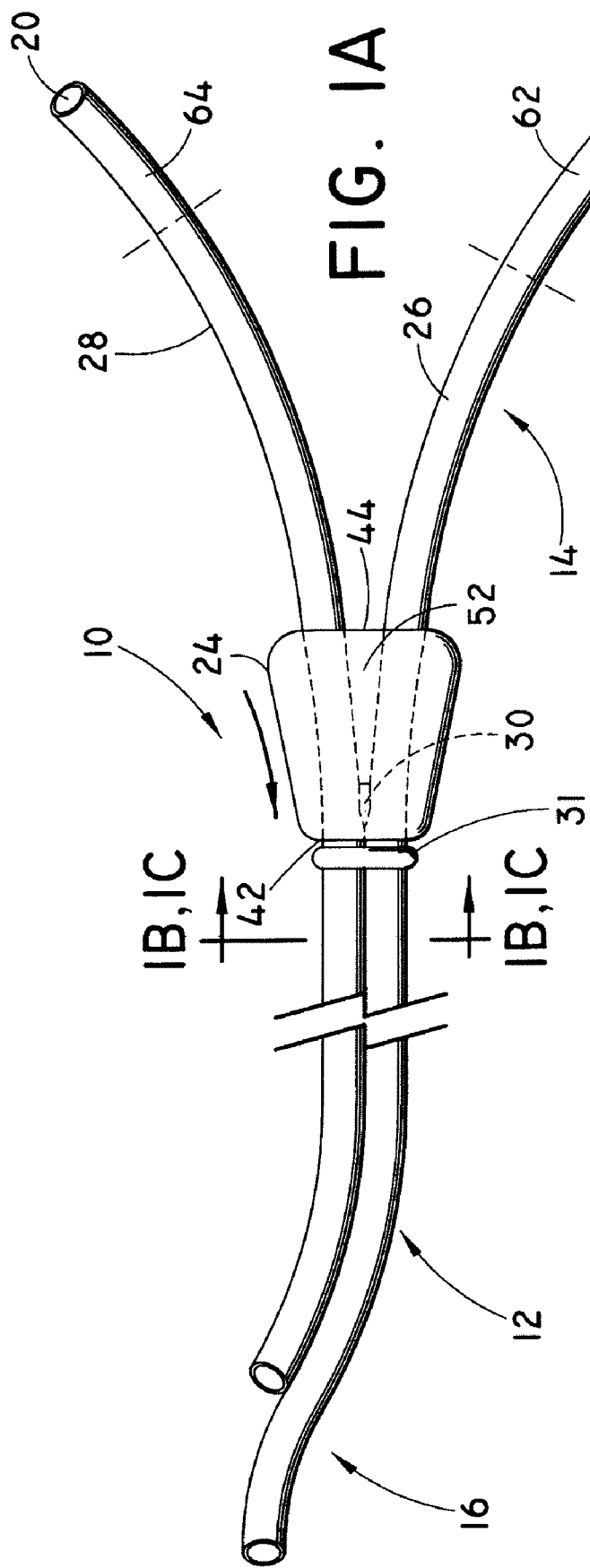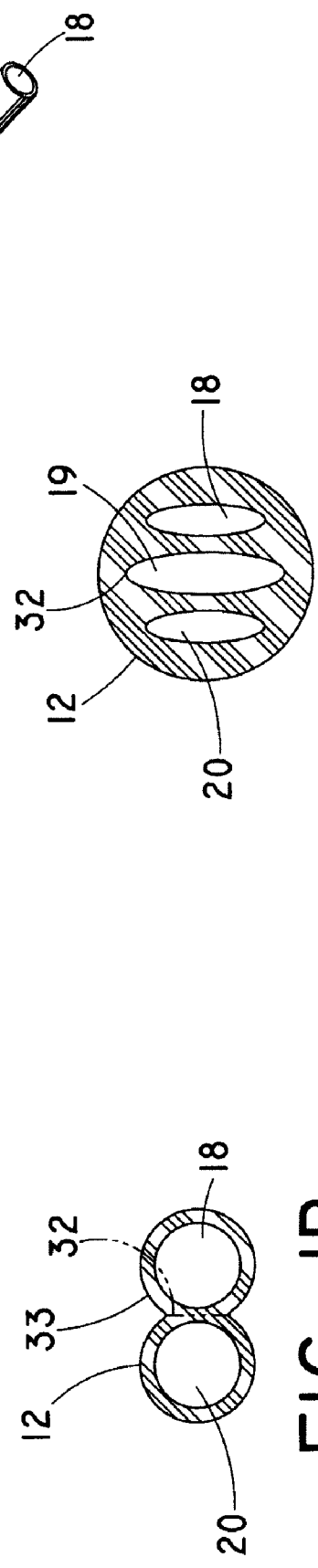

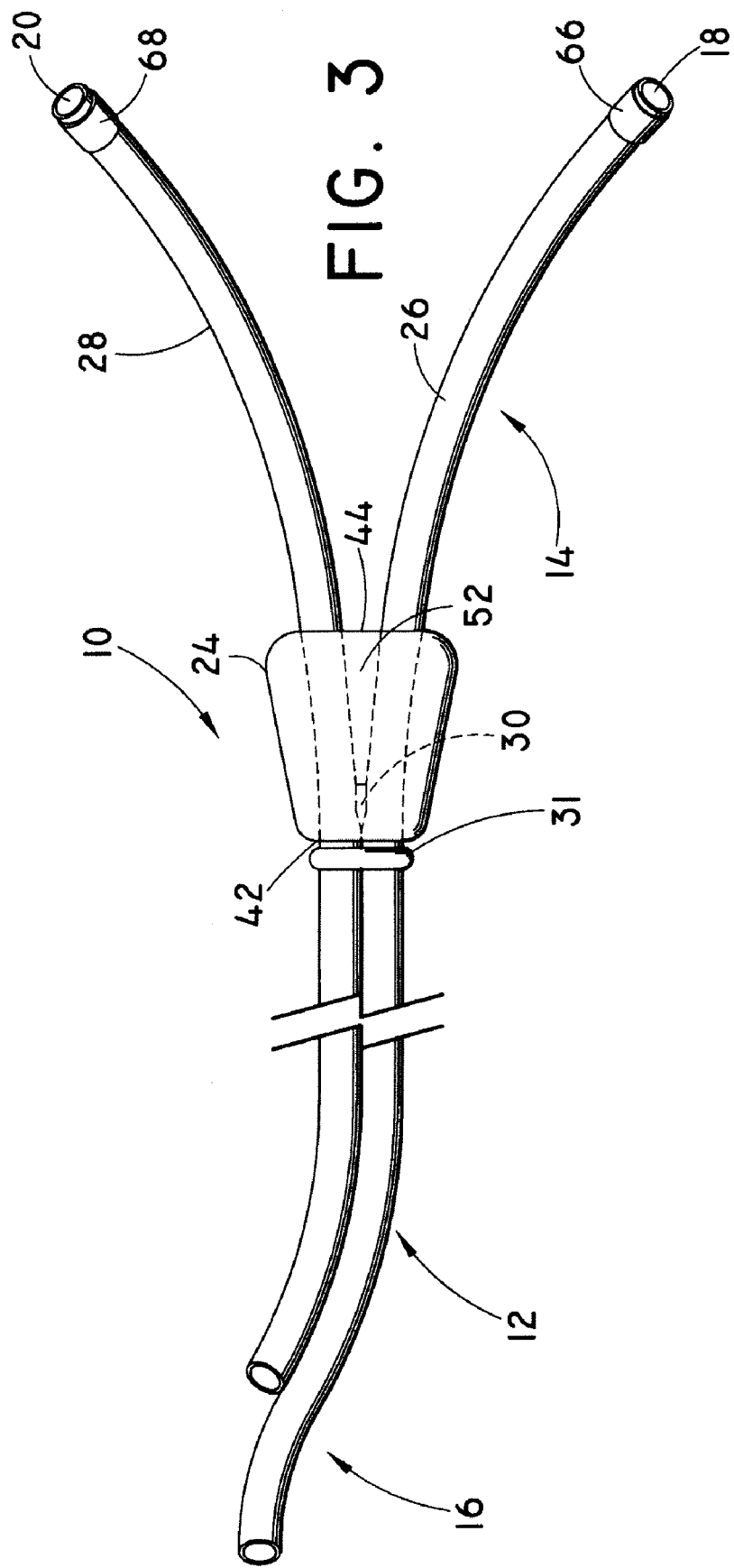

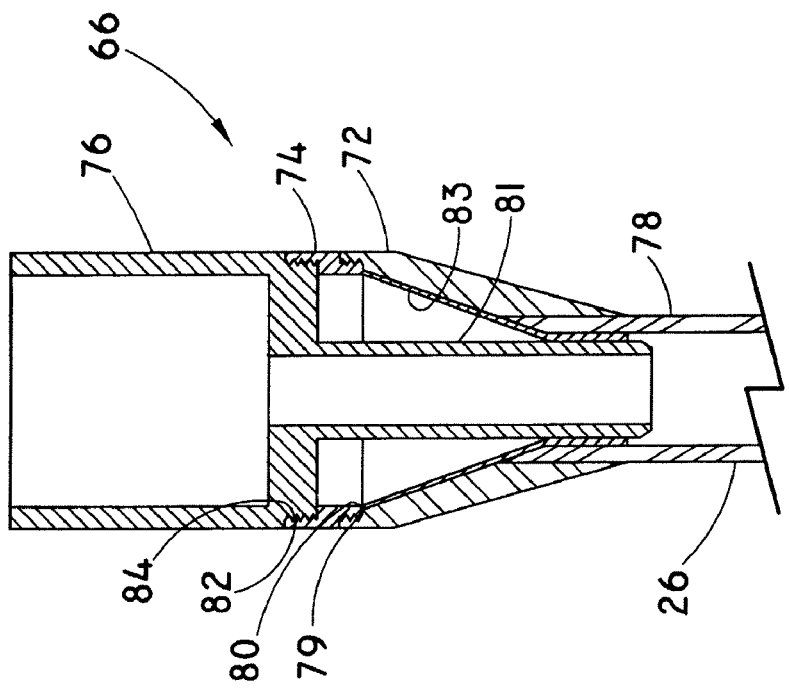
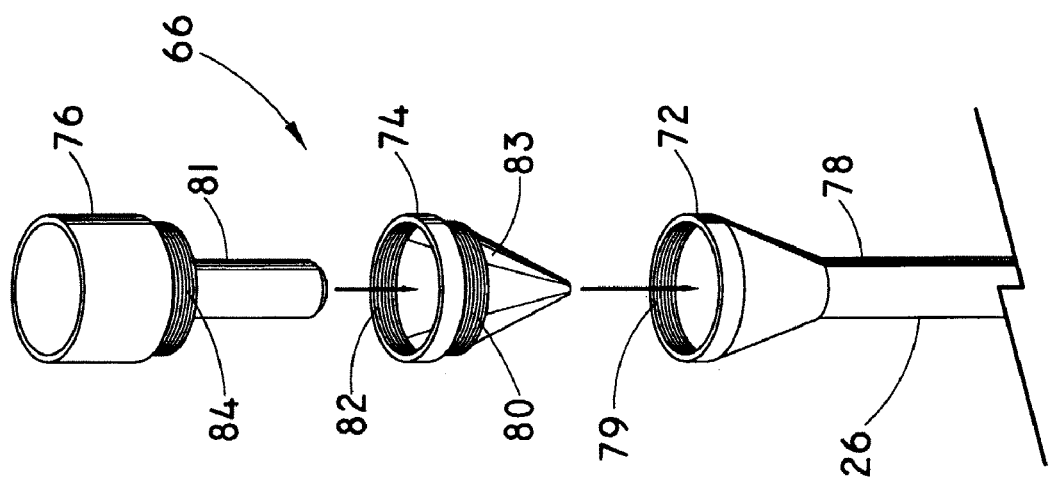

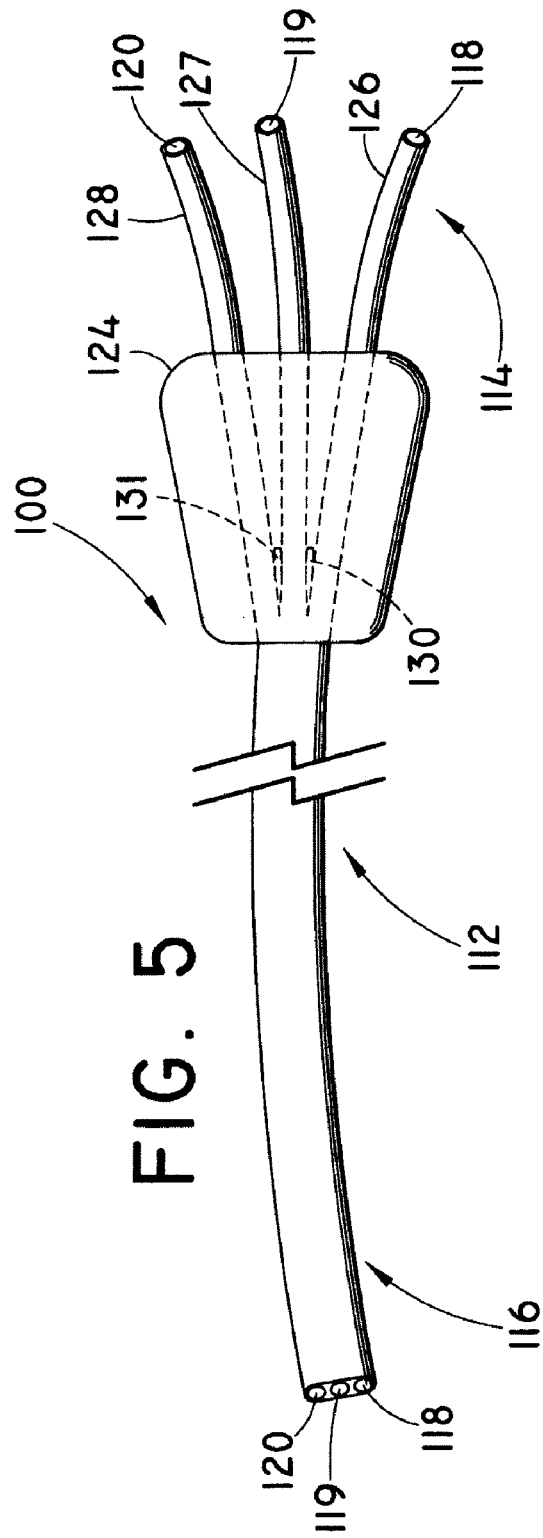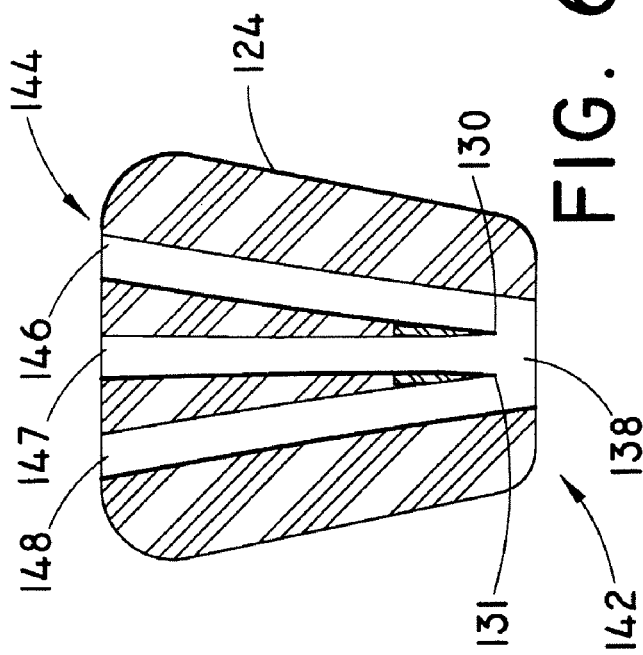

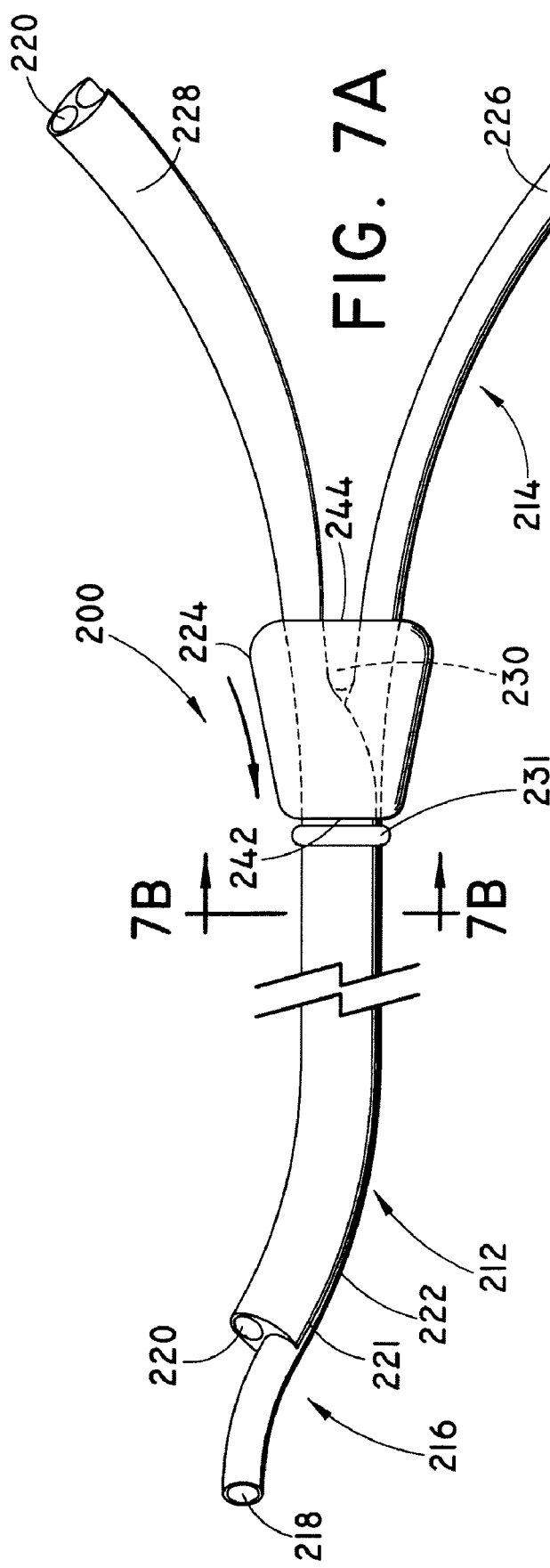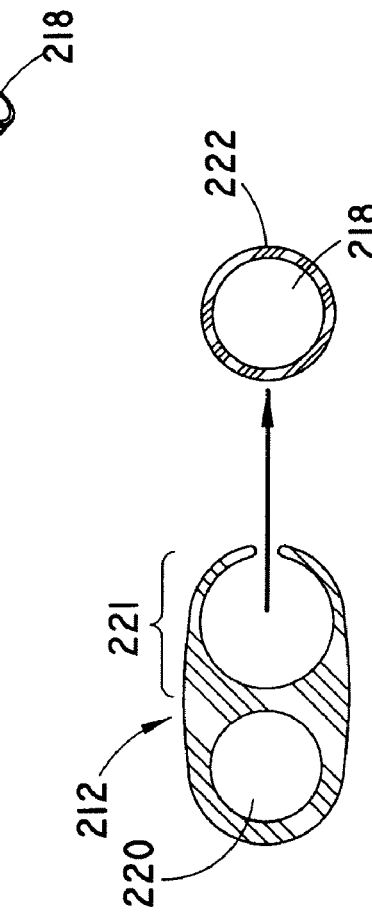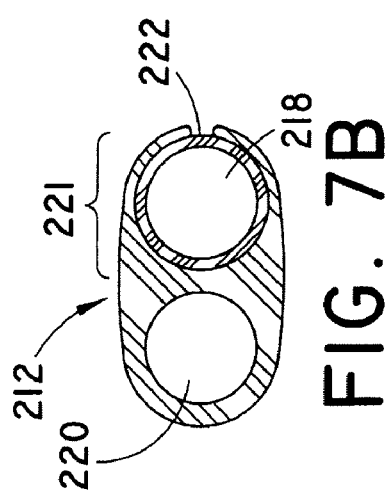

ADJUSTABLE LENGTH CATHETER

TECHNICAL FIELD

This invention relates generally to medical devices, and in particular, to catheters having different length requirements.

BACKGROUND OF THE INVENTION

Catheters or other medical devices for placement into a patient are used for many procedures. In certain procedures, precise placement of the distal tip of the device within the patient is critical. Physicians select from a variety of lengths of devices depending on the procedure to be performed and the specific patient requirements. Once the proper length device is selected, the device may be inserted into the patient and the distal tip located at the proper site. The device may include a proximal end that remains external to the patient and a portion that is subcutaneously tunneled before exiting the patient. The length of the proximal external portion of the device is also important for performing the proper procedure and for patient comfort.

For example, a patient may require a hemodialysis catheter that is typically inserted partially within the body with the distal end placed in a blood vessel and the proximal end external to the body and connectable to another device such as a dialysis unit. The hemodialysis catheter remains implanted within the patient for several treatments and avoids the need to have repeated needle insertions into the skin to gain access to the vasculature each time a dialysis procedure is initiated. The hemodialysis catheter should be of sufficient length so that the distal end of the hemodialysis catheter is properly placed within the vasculature to allow effective dialysis and allow for subcutaneous tunnel, and the proximal end(s) connectable to the treatment unit. The proximal end(s) of the hemodialysis catheter should also be of proper length to extend from the patient and have a fitting on the proximal end of the catheter accessible for connection to a treatment device, but not so long that the proximal end of the catheter gets entangled and torn away from the implantation site.

Currently, hospitals stock a large inventory of different types of catheters and other devices in various lengths so that the properly sized device is available for each individual patient and each procedure. Having such a large inventory of the devices in all different lengths adds to the expense of medical treatments and requires extensive inventory control. In addition, some devices for implantation into a patient have a limited shelf life. Depending on the frequency of procedures and the sizes required, some devices may exceed the useful shelf life before being used in a procedure. Expired devices also add to the expense of the patient care.

What are needed are a system and a method for making adjustable length devices, such as catheters, that can be implanted into the patient and adjusted to the proper length such that the devices may be universally used instead of requiring specific length devices. The adjustable length devices may be used similarly to the specific length devices in that the distal tip of the device is properly placed in the patient and the proximal end of the device may be adjusted in length to accommodate the patient needs and the specific procedure.

BRIEF SUMMARY OF THE INVENTION

The foregoing problems are solved and a technical advance is achieved in an illustrative medical device having an adjustable length and being suitable for implantation into a patient to meet the requirements of a specific length for a procedure and patient size.

In one aspect of the invention, an adjustable length catheter device for fluid flow therethrough is provided. The catheter device includes an elongate shaft having a proximal portion, a distal portion, a first lumen and a second lumen extending at least partially therethrough. The catheter device further includes a manifold operably connected to the shaft. The manifold is configured to longitudinally move along the shaft towards the distal portion for separating the proximal portion of the shaft into a first proximal shaft portion including the first lumen and a second proximal shaft portion including the second lumen.

In another aspect of the present invention, a method of providing an adjusted length catheter device to a patient is provided. The method includes inserting a distal portion of an elongate shaft into a vessel of the patient. The catheter device includes a first lumen and a second lumen extending at least partially through the elongate shaft and a manifold operably connected to the catheter device. The method further includes longitudinally moving the manifold along the shaft towards the distal portion. The method includes separating a proximal portion of the shaft into a first proximal shaft portion including the first lumen and a second proximal shaft portion including the second lumen and removing end portions from the first proximal shaft portion and the second proximal shaft portion to adjust the length of the device. The catheter device may be inserted into the patient vessel before or after removing the end portions from the first proximal shaft portion and the second proximal shaft portion to adjust the length of the device.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF SEVERAL VIEWS OF THE DRAWINGS

FIG. 1A is a side elevational view of an embodiment of a catheter device of the present invention;

FIG. 1B is a cross-sectional view taken along line 1B-1B shown in FIG. 1A;

FIG. 1C is a cross-sectional view of an alternative embodiment of the catheter device shown in FIG. 1A;

FIG. 3 is a side elevational view of the embodiment shown in FIG. 1A including fittings at the proximal portion;

FIG. 4A is an exploded view of a fitting shown in FIG. 3;

FIG. 4B is a side sectional view of the fitting shown in FIG. 3;

FIG. 5 is a side elevational view of an alternative embodiment of a catheter device of the present invention;

FIG. 6 is an enlarged sectional view of a manifold shown in FIG. 5;

FIG. 7A is a side elevational view of an alternative embodiment of a catheter device of the present invention;

FIG. 7B is a cross-sectional view taken along line 7B-7B shown in FIG. 7A;

FIG. 7C is a cross-sectional view of a first proximal shaft portion and a second proximal shaft portion;

DETAILED DESCRIPTION OF THE INVENTION

Figure 2A:
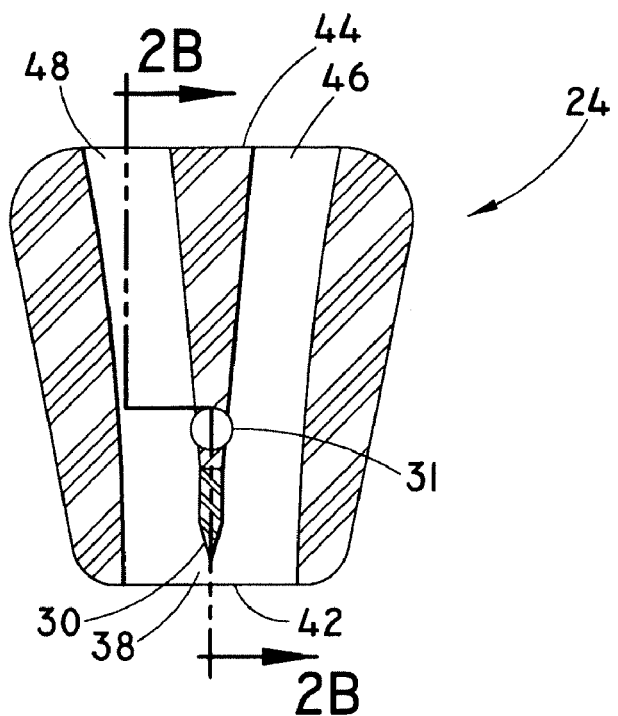
FIG. 2A is an enlarged sectional view of a manifold shown in FIG. 1A.

Several possible embodiments of a medical device of the present invention are shown in the figures. The medical device of the present invention may be any kind of medical device used for patient treatments needing a specific length device. Medical devices of the present invention include, but are not limited to, devices for treatment of the vasculature, urogenital system, and the gastrointestinal system. FIGS. 1A and 1B illustrate the present invention with reference to a hemodialysis catheter, however the description is intended to be illustrative of the present invention and not limited to such devices. The terms "proximal" and "distal" as used herein to describe the portions of the catheter. The term "proximal portion" refers the portion of the device that is closest to the operator during use of the medical device. The term "distal portion" refers to the portion of the device that is inserted into the patient, or that is closest to the patient.

A catheter device 10 of the present invention is shown in FIG. 1A. The catheter 10 includes an elongate shaft 12 having a proximal portion 14 and a distal portion 16. As shown in FIGS. 1A and 1B, the shaft 12 includes a first lumen 18 and a second lumen 20 extending through the shaft 12 from the proximal portion 14 to the distal portion 16. The lumens 18 and 20 are shown in a cross-sectional view in FIG. 1B taken along line A-A shown in FIG. 1A. The catheter device 10 may further include a manifold 24 operably connected to the shaft 12. The manifold 24 may be configured to be longitudinally slidable along the shaft 12 to separate the proximal portion 14 into a first proximal shaft portion 26 and a second proximal shaft portion 28 as the manifold 24 slides toward the distal portion 16 of the shaft 12. The manifold 24 may include a separator 30. As shown in FIG. 1A, the separator 30 separates the shaft 12 into the first proximal shaft portion 26 and the second proximal shaft portion 28 between the lumens 18 and 20 along a center portion 32 of the shaft 12 (shown in FIG. 1B). In some embodiments, and as illustrated in the alternative embodiment shown in FIG. 1C, the shaft 12 may include a third lumen 19 through the center portion 32 of the shaft 12 to facilitate separation of the shaft 12 at the central portion 32. The shaft 12 shown in FIG. 1C may be separated through the lumen 19 into the first proximal shaft portion 26 and the second proximal shaft portion 28 (FIG. 1A).

An end 62 of the first proximal shaft portion 26 and an end 64 of the second proximal shaft portion 28 may be removed from the catheter device 10 for obtaining the proper length device 10. Fittings may be added to the remaining first proximal shaft portion 26 and second proximal shaft portion 28 as described in detail below. In some embodiments, an exterior surface 33 of the shaft 12 may be contoured to facilitate alignment of the shaft 12 in the manifold 24, as shown in FIG. 1B. In other embodiments, the exterior surface may be smooth (FIG. 1C) or have an overlapping portion (FIG. 7B).

The catheter device 10 may also include a locking mechanism 31 to prevent the manifold 24 from further longitudinal sliding toward the distal portion 16 once the desired length for the catheter device 10 has been achieved. The locking mechanism 31 may be positioned on the shaft 12 at the appropriate distance from the proximal portion 14 to provide the catheter device 10 in the proper length. The locking mechanism 31 may be a clamp or any other type of member that prevents the manifold 24 from sliding further along the shaft 12 in the distal direction. In some embodiments, the locking mechanism 31 may be included on the manifold 24 to tighten the manifold 24 against the shaft 12 to prevent further distal sliding of the manifold 24 (described in more detail below).

A sectional view of the manifold 24 is shown FIG. 2A. The manifold 24 includes a first opening 38 for the shaft 12 at a distal portion 42 of the manifold 24. The separator 30 may be at the opening 38 or, alternatively, positioned proximal to the opening 38 so that the separator 30 is recessed within the manifold 24. The separator 30 may be any type of separation device, including, but not limited to, cutting element, such as a blade or a wire, or a portion of the manifold 24 that physically separates the first and second proximal portions 26 and 28 without cutting the shaft 12 as will be described in more detail below. A proximal portion 44 of the manifold 24 includes openings 46 and 48 sized and shaped to receive the first and second proximal shaft portions 26 and 28 after the shaft 12 has been longitudinally slid across the separator 30. The first and second proximal shaft portions 26 and 28 exit from the openings 46 and 48 of the manifold 24, respectively. In some embodiments, the separator 30 may be configured to be removable from the manifold 24 once the proper length for the catheter device 10 is obtained.

The manifold 24 may include the locking mechanism 31 as an alternative or in addition to the locking mechanism 31 shown in FIG. 1A on the shaft 12. In some embodiments, the locking mechanism 31 may be included on the manifold 24 and allow the manifold to slide distally on the shaft 12 until the desired catheter 10 length is reached. The locking mechanism 31 may be tightened against the shaft 12 without affecting the flow through the lumens 18 and 20 once the desired length is reached. An exemplary locking mechanism 31 is shown in FIGS. 2A-2E as a screw-type member 34 that extends through the manifold 24. The manifold 24 may be provided as a two-piece device that is held together by the locking mechanism 31 in a loosened configuration for allowing the manifold to slide distally along the shaft 12 so that the separating member 30 separates the shaft 12 into the first proximal shaft portion 26 and the second proximal shaft portion 28. Once the desired length for the catheter device 10 is reached, the locking mechanism 31 can be tightened by turning a loop 41 provided on the locking mechanism 31 to tighten the manifold 24 against the shaft 12 to prevent further movement of the manifold 24 on the shaft 12. An exemplary screw-type locking mechanism 34 is illustrated in FIG. 2C and may include a threaded portion 43 for connecting to the manifold 24 and the loop 41 for tightening the manifold 24 on the shaft 12. The loop 41 may fold down against a groove 45 in the locking mechanism 34 so that the loop 41 may be recessed within the manifold 24. When the loop 41 is folded down, the locking mechanism 34 may be in a recess 47 within an exterior surface so that the locking mechanism 34 will not accidentally be loosened by movement of the loop 41 and the loop 41 will not irritate the patient' skin at the site adjacent the manifold 24.

Figure 2B:
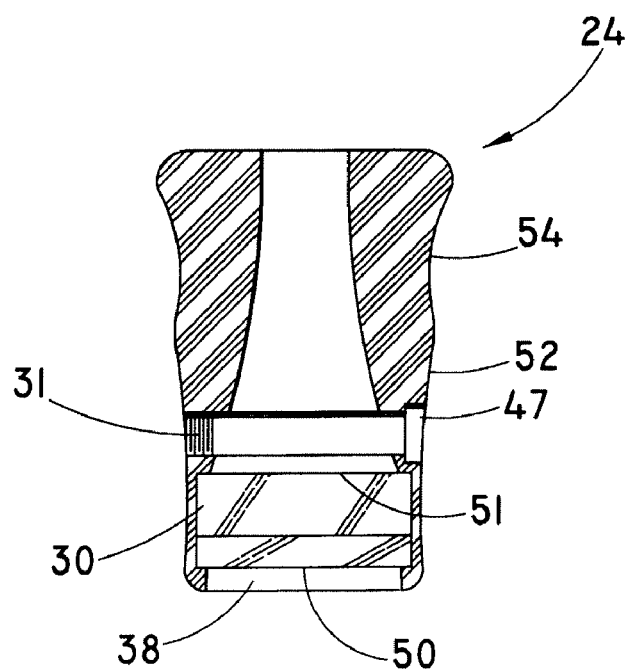
FIG. 2B is a side sectional view of the manifold shown in FIG. 2A.
Figure 2C:
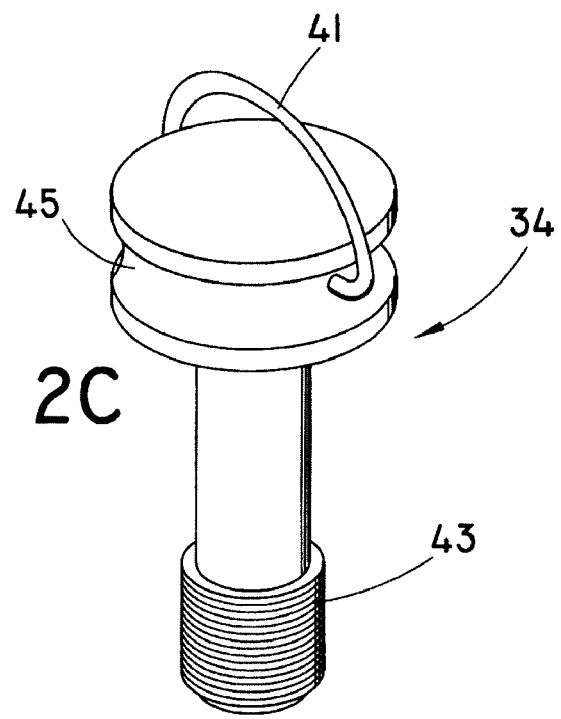
FIG. 2C is an enlarged perspective view of a locking mechanism shown in FIG. 2A.
Figure 2D:
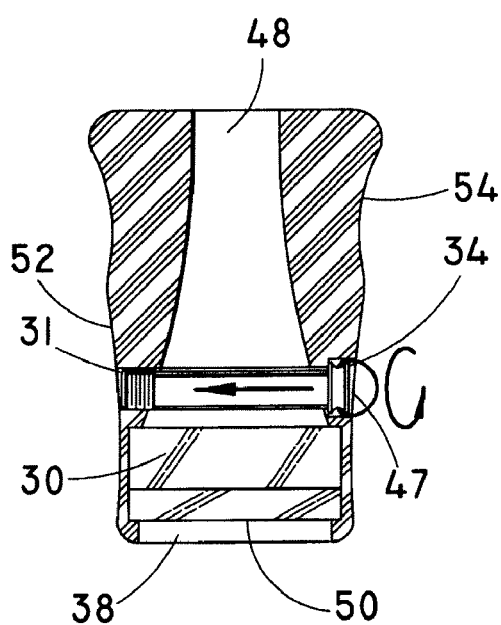
FIG. 2D is a side sectional view of the manifold shown in FIG. 2A with the locking mechanism included.
Figure 2E:
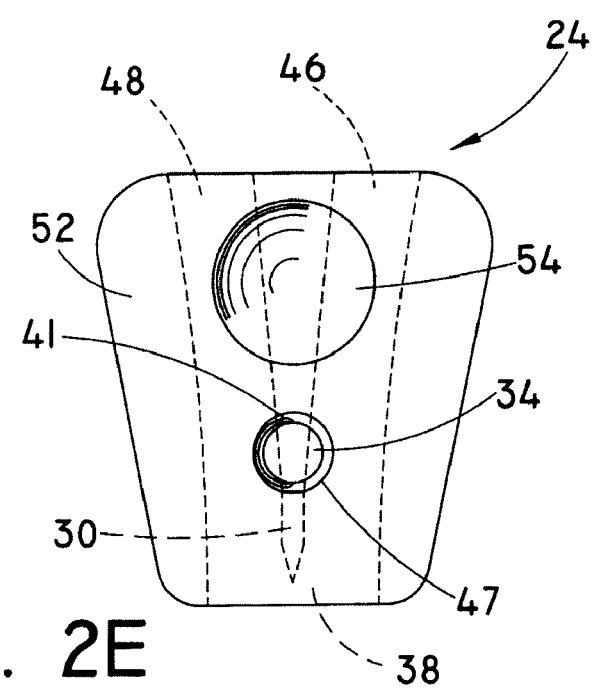
FIG. 2E is a top view of the manifold shown in FIG. 2A.

A side sectional view of the manifold 24 is shown in FIG. 2B taken along the line 2B-2B shown in FIG. 2A. As shown, the separator 30 may be a blade having a pointed distal tip 50 that is recessed with respect to the opening 38 to avoid accidental contact with the tip 50. The separator 30 is shown having a conical shape that expands to a proximal end 51 that has the same width as the central portion of the shaft 12 to be separated. Alternatively, the proximal end 51 may be wider than the central portion 32 of the shaft 12 to ensure separation of the first and second proximal shaft portions 26 and 28 of the shaft 12. The separator 30 may be any shape for separating first and second proximal shaft portions 26 and 28, including, but not limited to, triangular, rectangular, round, oval, serrated and the like. An exterior surface 52 of the manifold 24 may include one or more gripping portions 54 to facilitate longitudinal sliding of the manifold 24 with respect to the shaft 12 (See FIG. 1A). As will be understood by one skilled in the art, the separator 30 is capable of precise separation of the shaft 12 such that lumens 18 and 20 remain intact and sterile for use in the patient. In some embodiments, the manifold 24 may be removable from the shaft 12 once the desired length for the catheter device 10 has been obtained.

Fittings 66 and 68 may be connected to the first proximal shaft portion 26 and the second proximal shaft portion 28, respectively, after the ends 62 and 64 have been removed from the device 10, as shown in FIG. 3. The fittings 66, 68 may be any type of fitting suitable for connection with a treatment device (not shown). For example, the fittings 66, 68 may be a Luer lock or other suitable connector for engaging with a syringe or connector leading to the treatment device, such as a dialyzer or aspiration device.

An exemplary fitting 66 is illustrated in FIGS. 4A and 4B. The fitting 66 includes a cap 72, a sleeve 74 and an adapter 76. The cap 72 is sized and shaped to fit over an outer surface 78 of the proximal shaft portion 26. The cap 72 may include an internal connecting portion 79 such as threads, protrusions, and the like, inside the cap 72 for connection with the sleeve 74. The sleeve 74 may be expandable and insertable into an inner surface of the proximal shaft portion 26. The sleeve 74 includes an external connecting portion 80 that is configured to connect with the internal connecting portion 79 of the cap 72. For example, in some embodiments, the connection may be formed by mating threads on the cap 72 and the sleeve 74. In other embodiments, the cap 72 may include internal protruding members that snap-fit with indentations in the connecting portion 80 of the sleeve 74. In yet other embodiments, the cap 72 may be bonded to the sleeve 74, for example, using an adhesive.

The sleeve 74 may further include an internal connecting portion 82 for connecting with the adapter 76. The adapter 76 is insertable into the sleeve 74 and may include extension 81 for inserting into the cap 72 and an external connecting portion 84 for connecting with the internal connecting portion 82. For example, the external connecting portion 84 may be threaded and connecting to mating threads on the internal connecting portion 82 of the sleeve 74. Connecting the adapter 76 to the sleeve 74 may expand the sleeve 74 and compress the proximal shaft portion 26 within the fitting 66 so that a seal is created between the proximal shaft portion 26 and the fitting 66 for leak-free flow therethrough. The adapter 76 may be a Luer adapter or any type of adapter known in the art for connecting devices to a patient. The fitting 66 may also include a sealing device, such as a stopcock or cap, to seal the fitting 66 when the fitting 66 is not connected to any device. The fitting 66 described above is an exemplary type of fitting that may be used with the catheter device 10. A similar fitting may be connected to the second proximal shaft portion 28 or any shaft portion designed for connection to another device. Any type of fitting known to one skilled in the art and suitable for patient treatment may be used for connecting the proximal shaft portions to a treatment device and for sealing the proximal shaft portions when the catheter device is not connected to a treatment device.

The shaft 12 may include two, three, four or more lumens extending longitudinally through the shaft 12 between the proximal portion 14 and the distal portion 18. The lumens may be any size and shape and be designed for any type of delivery to or from the patient. The lumens may be of different sizes or shapes or both to distinguish the lumens from each other. Alternatively, the first proximal shaft portion 26 and the second proximal shaft portion 28 may have different colors or markings to distinguish the first and second shaft portions from each other when the lumens therethrough have different functions. By way of non-limiting example, when the catheter device is a hemodialysis catheter, the lumen 18 through the first proximal shaft portion 26 may be an infusion lumen and the lumen 20 through the second proximal shaft portion 28 may be an aspiration lumen. The shaft portions 26 and 28 may have different external marking so that when fittings 66 and 68 are connected to the shaft portions 26 and 28, the proper connections will be made to the treatment device.

The manifold 24 may include a corresponding number of openings at the proximal end 44 of the manifold 24 for the number of lumens to be separated in the shaft 12. The size and shape of the openings correspond to the size of the separated proximal portions of the shaft 12. The appropriate number of separators may also be included, i.e., one separator for dual lumen catheters, two separators for triple lumen catheters, etc. Each proximal shaft portion may include a marking so that when the shaft portions are separated through the manifold, each lumen may be distinguished.

An exemplary triple lumen catheter device 100 is shown in FIG. 5. Similar to the catheter device 10, the catheter device 100 includes an elongate shaft 112 having a proximal portion 114 and a distal portion 116. The shaft 112 includes a first lumen 118, a second lumen 119 and a third lumen 120 extending through the shaft 112 from the proximal portion 114 to the distal portion 116. The catheter device 100 may further include a manifold 124 operably connected to the shaft 112. The manifold 124 may be configured to be longitudinally slidable along the shaft 112 to separate the proximal portion 114 into a first proximal shaft portion 126, a second proximal shaft portion 127 and a third proximal shaft portion 128 as the manifold 124 slides toward the distal portion 116 of the shaft 112. The manifold 124 may include a first separator 130 and a second separator 131. Similar to the manifold 24 described above, the separators 130, 131 of the manifold 124 separate the shaft 112 at central regions (not shown) of the shaft 112 between the lumens 118, 119, 120.

A sectional view of the manifold 124 is shown FIG. 6. The manifold 124 includes a first opening 138 for the shaft 112 at a distal portion 142 of the manifold 124. The separators 130, 131 may be at the opening 138 or, alternatively, positioned proximal to the opening 138. A proximal portion 144 of the manifold 124 includes openings 146, 147 and 148 sized and shaped to receive the first, second and third proximal shaft portions 126, 127 and 128 after the shaft 112 has been longitudinally slid across the separators 130, 131. The first, second and third proximal shaft portions 126, 127 and 128 exit the openings 146, 147 and 148 of the manifold 124, respectively.

Another alternative embodiment of a catheter device 200 is shown in FIGS. 7A-7C. The catheter device 200 is similar to the catheter device 10 described above, but differs in the configuration of a shaft 212. Similar to the catheter device 10, the catheter device 200 includes the shaft 212 having a proximal portion 214 and a distal portion 216. As shown in FIG. 7A, the shaft 112 includes a first lumen 218 and a second lumen 220 extending through the shaft 212 from the proximal portion 214 to the distal portion 216. As shown in FIGS. 7B and 7C, the shaft 212 includes a first shaft section 221 and a second shaft section 222. The first shaft section 221 overlaps the second shaft section 222 to form a C-shaped holder for the second shaft section 222. The first and second shaft sections 221, 222 fit together to form the shaft 212. The catheter device 200 may further include a manifold 224 operably connected to the shaft 212. The manifold 224 may be configured to be longitudinally slidable along the shaft 212 to separate the proximal portion 214 into a first proximal shaft portion 226 formed from the first shaft section 221 and a second proximal shaft portion 228 formed from the second shaft section 222. The manifold 224 may be used to separate the shaft 212 by longitudinally sliding the manifold 224 toward the distal portion 216 of the shaft 212. The manifold 224 may include a separator 230 to separate the first proximal shaft portion 226 from the second proximal shaft portion 228 without cutting the shaft 212. In some embodiments, the separator 230 may be a protrusion in the manifold 224 that inserts into the C-shaped overlapping portion 223 of the second shaft section 221 (shown in FIG. 7C) to separate the first proximal portion 226 from the second proximal portion 228 as the portions 226, 228 exit from a proximal end 244 of the manifold 224. The catheter device 200 may further include a locking mechanism 231 for preventing the manifold 224 from sliding distally on the shaft 212 once the proper length for the catheter device 200 has been obtained.

Figure 8A:
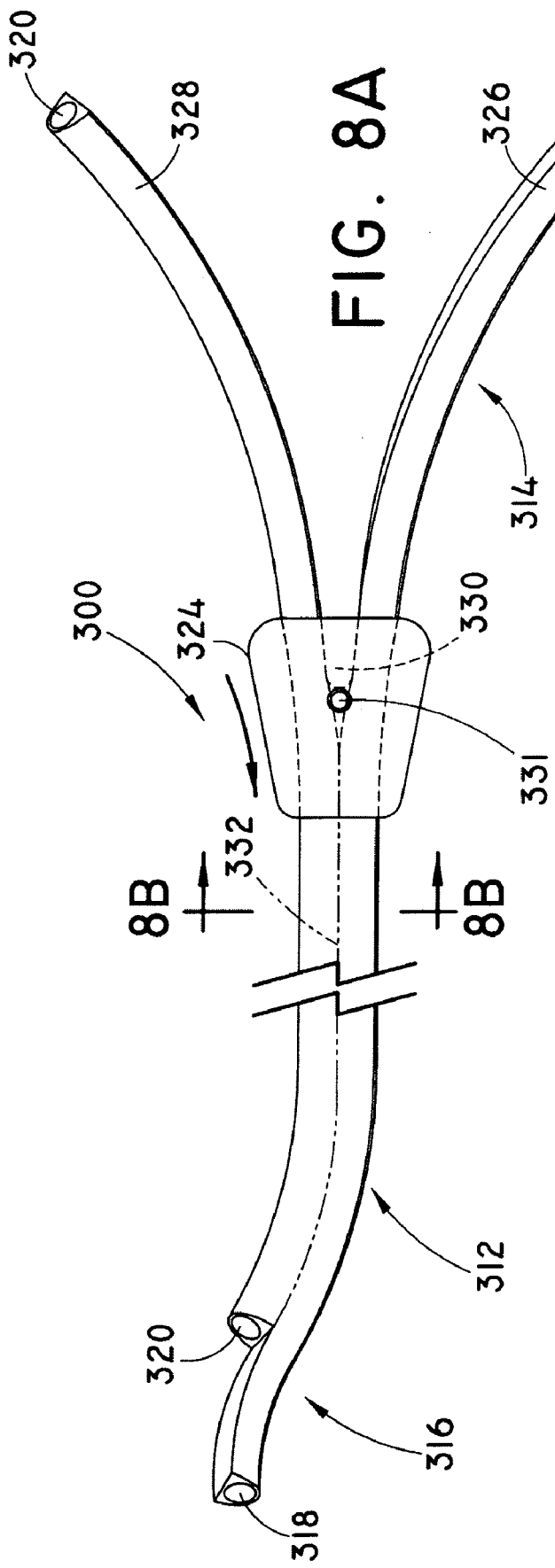
FIG. 8A is a side elevational view of an alternative embodiment of a catheter device of the present invention.
Figure 8B:
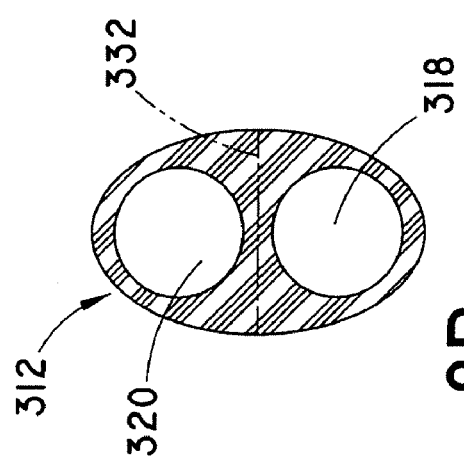
FIG. 8B is a cross-sectional view taken along line 8B-8B shown in FIG. 8A.

Another alternative embodiment of a catheter device 300 is shown in FIGS. 8A and 8B. The catheter device 300 is similar to the catheter device 10 described above and differs in the configuration of a central region 332 of a shaft 312. Similar to the catheter device 10, the catheter device 300 includes the shaft 312 having a proximal portion 314 and a distal portion 316. As shown in FIG. 8A, the shaft 312 includes a first lumen 318 and a second lumen 320 extending through the shaft 312 from the proximal portion 314 to the distal portion 316. The catheter device 300 may include a manifold 324 operably connected to the shaft 312 and the manifold may include a locking mechanism 331. The manifold 324 may be configured to be longitudinally slidable along the shaft 312 to separate the proximal portion 314 of the shaft 312 into a first proximal shaft portion 326 and a second proximal shaft portion 328. The central region 332 of the shaft 312 may be frangible, perforated or otherwise splittable to facilitate separation of the shaft 312 into the first and second proximal shaft portions 326, 328. The central region 332 is shown in FIG. 8B in a cross-sectional view taken along lines 8B-8B shown in FIG. 8A. The manifold 324 may be used to separate the shaft 312 by longitudinally sliding the manifold 324 toward the distal portion 316 of the shaft 312. The manifold 324 may include a separator 330 to separate the first proximal shaft portion 326 from the second proximal shaft portion 328 that may be a wedge-shaped portion of the manifold 324. The shaft 312 may be separated without using a blade or wire separator for separation. The locking mechanism 331 may be used to prevent the manifold 324 for further movement along the shaft 312 once the proper length for the catheter device 300 has been obtained.

The catheter device of the present invention may be any size suitable for treatment of a patient. By way of non-limiting example, a hemodialysis catheter may be between about 7 Fr and about 16 Fr and have a length of about 10 cm to about 100 cm. As will be understood by one skilled in the art, other sizes may also be used.

If desired, various components of the catheter devices and components described herein can be impregnated or coated with antimicrobial agents to minimize the risk of bacterial colonization of the catheter, and catheter-related bacteremia during use. An example of an antimicrobial combination that has been shown to be an effective antimicrobial composition in percutaneous devices is the combination of antimicrobials minocycline and rifampin. Alternatively, other well-known antimicrobials may be substituted for minocycline and rifampin, which antimicrobials need not necessarily be utilized in combination Operation of the adjustable catheter device of the present invention will be described with reference to the catheter device 10 shown in FIG. 1A. In some embodiments, the catheter device 10 may be supplied with the manifold 24 operably connected to the shaft 12. Separation of the shaft 12 may be initiated with the connection of the manifold 24 to the shaft 12 so that the first and second proximal shaft portion 26, 28 are separated in the proximal portion 44 of the manifold 24. In some methods of operation, the catheter device 10 may be introduced into the vessel of the patient. Suitable percutaneous techniques for insertion of catheter devices into body vessels are well known in the medical arts, and are in widespread use. Perhaps the most widely-utilized technique, and the technique favored herein, is the well-known Seldinger technique. In the Seldinger technique, an injection is made into the vessel interior with a needle, and a wire guide is inserted into the vessel through a bore in the needle. The needle is withdrawn, and an introducer sheath, preferably a splittable sheath, such as a PEEL-AWAY® splittable sheath, available from Cook Incorporated, of Bloomington, IN, is introduced over the wire guide. The catheter device is then introduced into the vessel via the introducer sheath and over the wire guide. The wire guide and the sheath are removed in conventional fashion, leaving at least the distal portion 16 of catheter device 10 in the body vessel.

Once the catheter device 10 has been inserted into a body vessel, and the distal portion 16 placed in the proper position in the patient, the physician may adjust the catheter device to the desired length for the procedure. The manifold 24 may be slid along the shaft 12 toward the distal portion 16. The gripping portion 54 of the manifold 24 may be used to facilitate movement of the manifold 24. As the manifold 24 moves distally along the shaft 12, the separator 30 separates the shaft 12 into the first and second proximal shaft portions 26, 28. The first and second shaft portions 26, 28 extending out from the proximal end 44 of the manifold 24 lengthen as the manifold moves distally. Once the desired length for the catheter device 10 is obtained, the manifold 24 may be prevented from further movement along the shaft 12 by the locking mechanism 31. For example, when the locking mechanism 31 comprises a clamp, the clamp may be secured to the shaft 12 by the physician using a clamping device. Alternatively, when the locking mechanism 31 comprises a screw-type mechanism, the manifold may be secured by tightening the screw using threads 43 by turning the loop 41 until the manifold 24 is secured on the shaft 12. The loop 41 may be folded down into the groove 45 and secured against the manifold 24. In some methods, the separator 30 or the manifold 24 may be removed from the catheter device 10 when the proper length has been obtained. In some embodiments, a standard manifold known in the art may be operably connected to the shaft 12 after the manifold 24 is removed.

By way of non-limiting example, the physician may select the device 10 having a length of about 40 cm from the distal end of the device 10 to the manifold 24. The physician plans to insert the device 10 about 30 cm and include a subcutaneous tunnel of about 5 cm near the manifold. To adjust the length of the device 10, the manifold 24 may be slid along the shaft 12 toward the distal portion 16 for about 5 cm to adjust the length of the catheter device 10 to about 35 cm allowing for about 30 cm to be inserted into the vasculature and about 5 cm to be subcutaneously tunneled. The excess proximal ends 62 and 64 may be left extending from the manifold or trimmed as described below. Additional lengths of the device 10 may be similarly adjusted to the appropriate length for the patient and the procedure.

The ends 62, 64 of the first and second proximal shaft potions 26, 28 may be removed from the catheter device 10 to provide the proper length for the device 10. The ends 62, 64 may be removed by cutting, heating or any method known to one skilled in the art for removing a portion of the shaft of a catheter device. Fittings 66, 68 may be connected to the remaining first and second proximal shaft portions 26, 28. The catheter device 10 may be connected to a treatment device suitable for treating the patient though the catheter device 10 that has been adjusted to the proper length. Once the treatment is completed, clamps (not shown) or the fittings may be closed to seal the catheter device until the next treatment. The treatment process may be repeated several times using the same catheter device 10. The device 10 may include a patient attachment portion on the manifold or suture wings known in the art that may be separate from the manifold to secure the device 10 to the patient once the device 10 has been adjusted to the appropriate length and implanted. For example, an attachment portion 351 is shown on the manifold 324 in FIG. 8A In some embodiments, the catheter device 10 may be adjusted to the appropriate length using the manifold 24 as discussed above and the fittings added before the catheter device 10 is inserted into the patient. Adjustment of the catheter device 10 is similar to the method describe above. The adjusted length catheter device 10 is then inserted into the patient using the technique described above or any suitable technique known in the art.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. The scope of the invention is defined by the appended claims, and all devices that come within the meaning of the claims, either literally or by equivalence, are intended to be embraced therein.

The invention claimed is:

1. An adjustable length catheter device for fluid flow therethrough, the catheter device comprising:
   an elongate shaft having a proximal portion and a distal portion, and further having a first lumen and a second lumen extending at least partially therethrough; and
   a manifold movably connected to the shaft, the manifold comprising a contacting portion including a separator device comprising a cutting element that contacts a portion of the shaft between the first and second lumens, a first manifold lumen and a second manifold lumen extending at least partially through the manifold, the manifold having a first position and a second position relative to the shaft, the second position being distal to the first position, the manifold is longitudinally movable along the shaft from the first position to the second position to separate the proximal portion of the shaft into a first proximal shaft portion including the first lumen and a second, separate proximal shaft portion including the second lumen as the manifold moves distally to the second position.

2. The catheter device of claim 1, wherein the cutting element is recessed within the manifold.

3. The catheter device of claim 1, further comprising a locking mechanism configured for selectively preventing movement of the manifold relative to the shaft.

4. The catheter device of claim 3, wherein the manifold comprises the locking mechanism.

5. The catheter device of claim 1, further comprising fittings connectable to the first proximal shaft portion and the second proximal shaft portion.

6. The catheter device of claim 5, wherein each fitting comprises a cap, a sleeve and an adaptor.

7. The catheter device of claim 1, wherein the shaft comprises a first shaft section and a second shaft section, wherein the first shaft section overlaps the second shaft section.

8. The catheter device of claim 1, wherein the catheter device is a hemodialysis catheter and the first lumen comprises an infusion lumen and the second lumen comprises an aspiration lumen.

9. The catheter device of claim 1, wherein at least a portion of the device includes an antimicrobial coating.

10. An adjustable length catheter device for fluid flow therethrough, the catheter device comprising:
    an elongate shaft having a proximal portion and a distal portion, and further having a first lumen and a second lumen extending at least partially therethrough; and
    a manifold movably connected to the shaft, the manifold comprising a contacting portion that contacts a portion of the shaft between the first and second lumens, a first manifold lumen and a second manifold lumen extending at least partially through the manifold, the manifold having a first position and a second position relative to the shaft, the second position being distal to the first position, the manifold is longitudinally movable along the shaft from the first position to the second position to separate the proximal portion of the shaft into a first proximal shaft portion including the first lumen and a second, separate proximal shaft portion including the second lumen as the manifold moves distally to the second position,
    wherein the shaft comprises a central portion extending longitudinally along the shaft between the first lumen and the second lumen, the central portion being configured to facilitate separation of the shaft.

11. The catheter device of claim 10, wherein the central portion comprises a frangible portion.

12. The catheter device of claim 10, wherein the central portion comprises a central lumen.

* * * * *